United States Patent [19]

Iimuro et al.

[11] Patent Number: 4,950,806
[45] Date of Patent: Aug. 21, 1990

[54] PROCESS FOR CRYSTALLIZING ADDUCT OF BISPHENOL A WITH PHENOL

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 311,844

[22] Filed: Feb. 17, 1989

[30] Foreign Application Priority Data

Feb. 22, 1988 [JP] Japan .................................. 63-37519
Feb. 22, 1988 [JP] Japan .................................. 63-37520

[51] Int. Cl.$^5$ ...................... C07C 37/84; C07C 37/68
[52] U.S. Cl. .................................. 568/724; 568/722; 568/727
[58] Field of Search ........................ 568/724, 722, 727

[56] References Cited

U.S. PATENT DOCUMENTS 2,791,616  5/1957  Luten, Jr. .............................. 568/724
4,529,823  7/1985  Mendiratta ........................... 568/724

FOREIGN PATENT DOCUMENTS 2758565  7/1978  Fed. Rep. of Germany ...... 568/724
1317648  1/1963  France ................................. 568/728
58-135832  8/1983  Japan ................................... 568/724

Primary Examiner—Werren B. Lone
Attorney, Agent, or Firm—Burns, Doane, Swecker & Mathis

[57] ABSTRACT

A process for crystallizing the adduct of bisphenol A with phenol from a phenol solution in the presence of water comprises controlling the concentration of bisphenol A in said solution by removing portion of the phenol from said solution or adding phenol to said solution according to feedback control based on the measurement of solution density to obtain an adjusted solution, and feeding the adjusted solution to the crystallizer in which its inside wall is kept at a temperature higher than that of the adjusted solution, provided the temperature difference being smaller than 5° C. The crystallized adduct has a uniform particle size and a high purity.

3 Claims, 1 Drawing Sheet

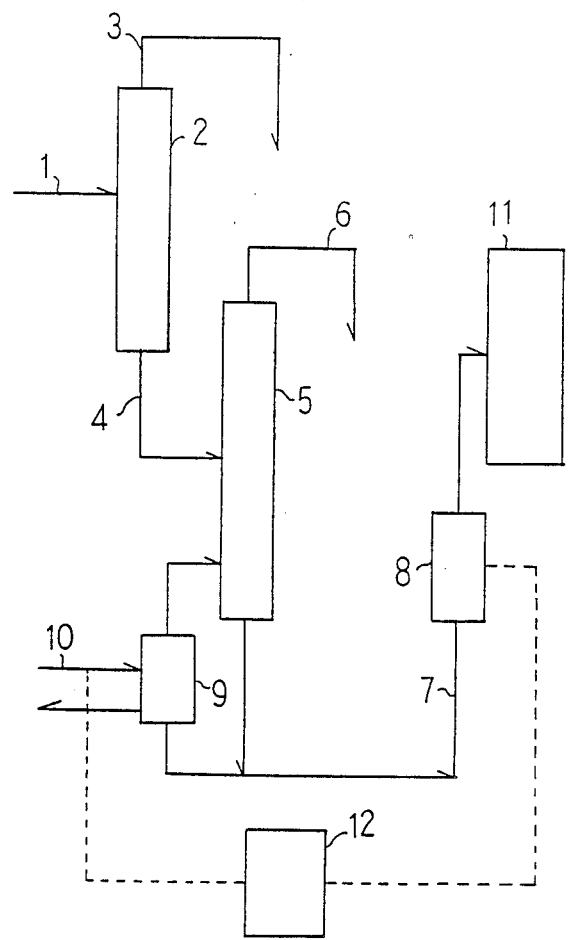

PROCESS FOR CRYSTALLIZING ADDUCT OF BISPHENOL A WITH PHENOL

BACKGROUND OF THE INVENTION

The present invention relates to a process for crystallizing the adduct of bisphenol A with phenol.

There is an increasing demand for bisphenol A as a raw material for polycarbonate resins and epoxy resins, particularly for engineering plastics. These applications need colorless and high-purity bisphenol A.

Bisphenol A is produced, for example, by reacting phenol with acetone in the presence of an acid catalyst, freeing the product mixture of the catalyst, water, unreacted acetone, and a small amount of phenol, cooling the remaining liquid mixture, thereby crystallizing the adduct of bisphenol A with phenol, separating the adduct crystals from the mother liquor, and removing phenol from the adduct, thereby obtaining bisphenol A.

In the case where the catalyst is hydrochloric acid, the product mixture is heated to 100 to 120° C. under reduced pressure for the removal of hydrochloric acid, unreacted acetone, water, and a small amount of phenol.

The vacuum distillation is usually accomplished by controlling the temperature of the bottom product and thus controlling the concentration of the bottom product, while keeping the operating pressure constant according to the vapor-liquid equilibrium of phenol and bisphenol A. (In this case, the bottom product is regarded as a binary system composed of phenol and bisphenol A.)

A disadvantage of this operating method is that the concentration control by means of the temperature control is practically difficult because the boiling point of the bottom product changes only a little even when the concentration of bisphenol A changes greatly. For example, the boiling point is 107° C., 108° C., 109° C., and 110° C. when the concentration of bisphenol A is 25 wt. %, 30 wt. %, 35 wt. %, and 40 wt. %, respectively, if the distillation pressure is 50 mm Hg. Therefore, it is difficult to keep constant the concentration of bisphenol A in the bottom product.

If the bottom product with fluctuating concentrations is continuously fed to a crystallizer, the amount of crystals that are produced in the crystallizer will fluctuate. This makes the quality of the adduct of bisphenol inconsistnet thereby A with phenol, adversely affecting the quality of bisphenol A.

In addition, the fluctuation of concentration leads to the great fluctuation of particle size. This, in turn, leads to the fluctuation of quality because the crystals carry the mother liquor containing impurities in the solid-liquid separating step, with the amount of the mother liquor carried varying depending on the particle size.

The fluctuating concentration of bisphenol A in the slurry poses another problem. An excessively low concentration leads to low yields. An excessively high concentration leads to an increased slurry viscosity, making the slurry transportation impossible.

A problem associated with the continuous crystallization is the deposit of scale on the inside wall of the crystallizer. The deposit of scale interrupts the operation of the crystallizer, making it impossible to produce crystals of uniform quality in a stable manner.

The crystallization of the adduct of bisphenol A with phenol may be accomplished by a process disclosed in Japanese Patent Laid-open No. 135832/1983. According to this process, heat including the heat of crystallization is removed by adding water and evaporating the water. It is considered that no scale easily deposits on the inside wall of the crystallizer because the heat of crystallization is removed internally. Incidentally, said Japanese patent describes nothing about lagging the crystallizer.

The deposit of scale in the crystallizer is usually prevented by providing the crystallizer with a lagging material or a jacket for hot water circulation. These provisions prevent the degree of supersaturation from excessively increasing on the inside wall. The deposit of scale is also prevented by providing the crystallizer with a scraper which removes the scale from the inside wall, or by adding a solvent which dissolves the scale. (See Chemical Engineering Handbook, 4th edition p. 453, published by the Japanese Chemical Industry Association.)

In the case where the adduct of bisphenol A with phenol is crystallized by adding water, providing the crystallizer with a jacket has a disadvantage that a large amount of vapor is generated when the jacket is kept at an excessively high temperature. This leads to an energy loss and makes it necessary to enlarge the equipment. In addition, this causes the vigorous vaporization and bumping of water, which disturb the crystal growth, resulting in the decreased purity and particle size of the crystallized adduct.

On the other hand, providing the crystallizer with a scraper has a disadvantage that the scraper crushes the crystals, making it difficult to separate the crystals in the subsequent solid-liquid separating step, and resulting in decreased quality (due to the mother liquor remaining on the crystal surface) and decreased yields.

Adding a solvent to prevent the deposit of scale is not economical because an additional apparatus is necessary for solvent recovery. In addition, the solvent added is liable to deteriorate the quality of the product.

SUMMARY OF THE INVENTION

It is an object of the present invention to provide a process for crystallizing the adduct of bisphenol A with phenol having a high purity, uniform quality, and uniform particle size in the presence of water, said process being free of the above-mentioned problems.

As a result of our extensive studies, it was found that said object is achieved when the concentration of bisphenol A in the phenol solution of bisphenol A to be fed to the crystallizer is controlled by a proper means and the temperature of the inside wall of the crystallizer is kept higher than that of the solution present in the crystallizer. The present invention was completed on the basis of this finding.

In accordance with the present invention there is provided a process for crystallizing the adduct of bisphenol A with phenol from a phenol solution of bisphenol A in the presence of water, said process comprising the steps of controlling the concentration of bisphenol A in said solution by removing a portion of the phenol from said solution or adding phenol to said solution according to feedback control based on the measurement of solution density to obtain an adjusted solution and feeding the adjusted solution to the crystallizer in which its inside wall is kept at a temperature higher than that of the adjusted solution, provided the temperature difference is smaller than 5° C.

BRIEF DESCRIPTION OF THE DRAWINGS

The accompanying drawing is a flowsheet showing an embodiment of the present invention.

DETAILED DESCRIPTION OF THE INVENTION

In the process of the present invention, the starting phenol solution of bisphenol A which has not undergone the adjustment of concentration may be a liquid mixture obtained by reacting phenol with acetone in the presence of an acid catalyst and then removing the catalyst, water, unreacted acetone, and a small amount of phenol from the product mixture. The phenol solution may also be a solution of crude bisphenol A in phenol.

For example, in the case where bisphenol A is synthesized by the aid of a strongly acidic cation-exchange resin as the catalyst, it is necessary to remove part of phenol from the phenol solution for the following reason. The synthesis in this case is usually accomplished by a fixed bed reaction which requires that the molar ratio of phenol to acetone in the starting reaction mixture should be high. (In other words, the reaction needs a large excess of phenol.) Therefore, the phenol solution obtained by removing acetone, water, and a small amount of phenol from the product mixture contains bisphenol A in a low concentration. Thus it is necessary to increase the concentration of bisphenol A by removing part of phenol from the phenol solution.

On the other hand, it is necessary to add phenol to a phenol solution in the case where the adduct of bisphenol A with phenol is dissolved in phenol and recrystallized from the phenol solution for further purification.

The density of a phenol solution of bisphenol A can be conveniently measured with a liquid densimeter of the in-line type. The densimeter should have an accuracy of 0.001 g/cm$^3$ because the density at 100° C. changes by 0.001 g/cm$^3$ as the concentration changes by 1 wt. %. For example, the density corresponding to the concentration of bisphenol A of 30 wt. %, 40 wt. %, and 50 wt. % is 1.040, 1.050, and 1.060 g/cm$^3$, respectively. This requirement will be met by an oscillating liquid densimeter which is commercially available.

The removal of phenol for the adjustment of concentration of bisphenol A may be accomplished by vacuum distillation which evaporates part of the phenol. In this case, the vacuum distillation should be performed by controlling the amount of steam to heat the reboiler in response, to the density of the bottom product. In other words, the feedback control should be performed by measuring the density of the solution.

The addition of phenol for the adjustment of concentration of bisphenol A may be accomplished by mixing the phenol solution of bisphenol A with phenol in a mixer. The adequate amount of phenol to be added should be established by measuring the density of the resulting mixed solution.

After the adjustment of the concentration, the solution should contain 20 to 50 wt. %, preferably 30 to 45 wt. %, of bisphenol A. With a concentration lower than 20 wt. %, the solution gives the product in low yields. Conversely, with a concentration higher than 50 wt. %, the solution gives a slurry of adduct which has such a high apparent viscosity that it cannot be transported.

After the adjustment of concentration, the phenol solution of bisphenol A is continuously fed to a crystallizer and discharged continuously. In the crystallizer, the solution is slowly stirred and cooled to a temperature in the range of 35 to 70° C., so that the adduct of bisphenol with phenol crystallizes.

This cooling is accomplished by adding water to the crystallizer and evaporating the water and a small amount of phenol to remove heat. The evaporation produces a distillate composed of water and a small amount of phenol. The distillate can be recycled.

The water should be added in an amount sufficient to remove heat by evaporation for cooling the phenol solution of bisphenol A and removing the heat of crystallization which is generated when the adduct crystallizes out. This amount of the water is equivalent to 2 to 20 wt. % of the phenol solution.

The crystallizer should be operated under a constant pressure, preferably 20 to 100 mm Hg. The temperature of the content can be controlled by adjusting the amount of water to be added to the crystallizer.

The inside wall of the crystallizer should be kept at a temperature higher than that of the contents of the crystallizer. This is accomplished by providing the crystallizer with a jacket and passing temperature-controlled hot water through it.

In the case where the crystallizer is of Draft-tube type, it is preferable that the tube also has a jacket.

If the temperature of the hot water is lower than that of the content in the crystallizer, the degree of supersaturation on the inside wall increases to such an extent that the adduct crystallizes on the inside wall. This makes it necessary to remove the scale periodically and prevents the stable operation of the process.

The temperature of the hot water should be controlled such that it does not differ more than 5° C. from that of the content. If the temperature difference is greater than 5° C., water evaporates vigorously at the vapor-liquid interface, and bumping and boiling occurs on the inside wall. These disturb the crystal growth and decrease the purity and particle size of the adduct crystals.

The process of the invention will be described with reference to the flowsheet shown in the accompanying drawing.

The product mixture 1, which has been obtained by reacting phenol with acetone in the presence of hydrochloric acid as the catalyst, is fed to a dehydrochlorination column 2. From the top of the column is discharged a mixture 3 of water, hydrochloric acid, and a small amount of phenol; and from the bottom of the column is discharged a mixture 4 of phenol, bisphenol A, and by-products.

The mixture 4 is fed to a phenol evaporator 5. From the top of the evaporator is discharged phenol 6, and from the bottom of the evaporator is discharged a phenol solution 7 of bisphenol A. In order that the phenol solution 7 of constant concentration is fed to a crystallizer 11, the phenol evaporator 5 is operated such that the density of the phenol solution 7 measured with a liquid densimeter 8 is equal to the set value. This is accomplished by controlling the amount of steam 10 to be fed to the reboiler 9 of the phenol evaporator 5. In deed, this control is accomplished by means of a steam amount controller responsive to the density. In the crystallizer, the adduct of bisphenol A with phenol crystallizes out. Incidentally, the crystallizer 11 is provided with a jacket for hot water.

EXAMPLES

The invention will be described in more detail with reference to the following examples, in which "%" means "wt. %", unless otherwise indicated.

EXAMPLE 1

The synthesis of bisphenol A was performed by blowing hydrogen chloride into a mixture of phenol and acetone at 55° C. for 8 hours. The product mixture was heated under reduced pressure in a dehydrochlorination column for the removal of hydrochloric acid and water formed by the reaction. The dehydrochlorinated solution contained 32 to 38% of bisphenol A, 2 to 5% of by-products and the balance being phenol.

Then, the dehydrochlorinated solution was fed to a phenol evaporator which was operated under a pressure of 50 mm Hg and at the bottom temperature of 110° C. in the phenol evaporator, the dehydrochlorinated solution was concentrated until the concentration of bisphenol A increased to 40% by removing part of phenol.

The removal of phenol was performed in response to feed-back control. In other words, the liquid densimeter (Liquid Densimeter Model 7830, SOLARTRON) was placed in the line between the phenol evaporator and the crystallizer, and the amount of steam to be fed to the reboiler of the phenol evaporator was controlled such that the density of the dehydrochlorinated solution measured with the liquid densimeter was equal to the set value. This control was accomplished by means of a steam amount controller responsive to the density.

From the phenol evaporator was discharged a phenol solution of bisphenol A at 90° C. The phenol solution was then fed at a flow rate of 400 kg/hr to a crystallizer which was operated under a pressure of 50 mm Hg.

The crystallizer was heated with hot water (52° C.) passing through the jacket. To the crystallizer was added water at a flow rate of 40 kg/hr via a separate route. The content in the crystallizer was maintained at a constant temperature of 50° C. The resulting slurry was continuously discharged from the crystallizer and then continuously filtered.

The crystallized adduct of bisphenol A with phenol had an average particle diameter of 0.4 mm and contained 0.05% of by-products. It gave a 50% ethanol solution having a Hazen color of 5 APHA.

During the operation, the concentration of bisphenol A in the dehydrochlorinated solution discharged from the dehydrochlorination column was not constant, whereas the concentration of bisphenol A in the dehydrochlorinated solution (feedstock for crystallization) entering the crystallizer was constant.

The entire process was run stably without any crystal growth on the inside wall of the crystallizer.

COMPARATIVE EXAMPLE 1

The adduct of bisphenol A with phenol was crystallized in the same manner as in Example 1, except that the liquid densimeter was not used (or the concentration of bisphenol A in the feedstock for crystallization was not controlled). Although the phenol evaporator was run under constant conditions, the concentration of bisphenol A in the feedstock for crystallization fluctuated between 35% and 45% because th concentration of bisphenol A in the dehydrochlorinated solution fluctuated. In addition, the temperature of the content in the crystallizer also fluctuated as the concentration of bisphenol A fluctuated.

The crystallized adduct of bisphenol A with phenol had an average particle diameter of 0.2 mm. It gave a 50% ethanol solution having a Hazen color of 20 APHA.

COMPARATIVE EXAMPLE 2

The adduct of bisphenol A with phenol was crystallized in the same manner as in Example 1, except that hot water at 48° C. was passed through the jacket and water was added at a flow rate of 35 kg/hr to the crystallizer. The content in the crystallizer remained constant at 50° C.

After the operation for one week, crystals grew into a large mass on the inside wall of the crystallizer, making continued operation impossible.

COMPARATIVE EXAMPLE 3

The adduct of bisphenol A with phenol was crystallized in the same manner as in Example 1, except that hot water at 57° C. was passed through the jacket and water was added at a flow rate of 50 kg/hr to the crystallizer. The content in the crystallizer remained constant at 50° C.

During the operation, the stirring was disturbed by vigorous water bumping, although no scale deposited.

To keep the level of the content in the crystallizer constant, the slurry was discharged continuously. The slurry contained a large amount of fine crystals having an average particle diameter of 0.2 mm. Upon the continuous filtration, the slurry gave crystals containing 0.2% of by-products.

The crystallized adduct gave a 50% ethanol solution having a Hazen color of 30 APHA.

According to the process of the present invention, it is possible to crystallize the adduct of bisphenol A with phenol in the presence of water in a stable manner. In addtion, the crystallized adduct has a uniform particle size and a high purity.

What is claimed is:

1. A process for crystallizing an adduct of bisphenol A with phenol from a phenol solution of bisphenol A in the presence of water, said process comprising the steps of controlling the concentration of bisphenol A in said solution by removing a portion of the phenol from said solution or adding phenol to said solution according to feedback control based on the measurement of solution density to obtain an adjusted solution containing from 20 to 50 wt. % of bisphenol A, and feeding the adjusted solution to the crystallizer to form a content solution having a temperature of 35 to 70° C. and maintaining the inside wall of the crystallizer at a temperature higher than that of the content solution, provided the temperature difference is smaller than 5° C.

2. A process as claimed in claim 1, wherein the adjusted solution contains 30 to 45 wt. % of bisphenol A.

3. A process as claimed in claim 1, wherein the crystallizer is of Draft-tube type and wall surfaces of the Draft-tube are also kept at a temperature higher than the temperature of the content solution, with the temperature difference being smaller than 5° C.

* * * * *